United States Patent
Curel et al.

(10) Patent No.: US 10,845,374 B2
(45) Date of Patent: Nov. 24, 2020

(54) DEVICE FOR THE STORAGE AND SELECTION OF PRE-FILLED CARTRIDGES OF REACTIVE DISCS

(71) Applicant: INTELLIGENCE ARTIFICIELLE APPLICATIONS, Montpellier (FR)

(72) Inventors: Christian Curel, Laverune (FR); Michel Roch, Saint Bres (FR); Jean-Louis Cariou, Aubais (FR)

(73) Assignee: INTELLIGENCE ARTIFICIELLE APPLICATIONS, Montpellier (FR)

( * ) Notice: Subject to any disclaimer, the term of this patent is extended or adjusted under 35 U.S.C. 154(b) by 322 days.

(21) Appl. No.: 15/523,094

(22) PCT Filed: Oct. 28, 2015

(86) PCT No.: PCT/FR2015/052900
§ 371 (c)(1),
(2) Date: Apr. 28, 2017

(87) PCT Pub. No.: WO2016/071604
PCT Pub. Date: May 12, 2016

(65) Prior Publication Data
US 2017/0315144 A1   Nov. 2, 2017

(30) Foreign Application Priority Data
Nov. 3, 2014   (FR) ..................................... 14 60562

(51) Int. Cl.
*G01N 35/02* (2006.01)
*B01L 3/00* (2006.01)
(Continued)

(52) U.S. Cl.
CPC ............ *G01N 35/025* (2013.01); *B01L 3/527* (2013.01); *C12M 23/48* (2013.01); *C12M 41/12* (2013.01);
(Continued)

(58) Field of Classification Search
CPC ................. G01N 35/025; G01N 35/04; G01N 2035/0045; G01N 2035/0443;
(Continued)

(56) References Cited

U.S. PATENT DOCUMENTS

2010/0288830 A1  11/2010  Watari
2012/0277905 A1*  11/2012  Botma ............... G01N 35/1002
                                                             700/236
2015/0198622 A1   7/2015  Botma et al.

FOREIGN PATENT DOCUMENTS

GB           2001432 A  *  1/1979  ......... G01N 35/1002
WO     WO-2006109005 A1 * 10/2006  ............ C12M 99/00

OTHER PUBLICATIONS

International Search Report dated Feb. 17, 2016.

* cited by examiner

*Primary Examiner* — Benjamin R Whatley
(74) *Attorney, Agent, or Firm* — Ipsilon USA, LLP

(57) ABSTRACT

A device is provided for the storage and selection of cartridges (20) that are pre-filled with reactive discs to be placed on a support. The support has a plurality of magazines (2) each able to store a cartridge (20) of discs, at least one magazine-holding support (3) and, for each support (3), drive means (4) for moving the magazine-holding support (3). The device (1) has a chamber (5) for housing at least one magazine-holding support (3). A drive mechanism (8) drives the movement of the magazine (2) in the placement configuration between a position in which said magazine (2) is distant from and a position in which same is closer to the placement opening (7) of the chamber (5).

14 Claims, 6 Drawing Sheets

(51) Int. Cl.
  *C12Q 1/18* (2006.01)
  *G01N 35/04* (2006.01)
  *C12M 3/00* (2006.01)
  *C12M 1/34* (2006.01)
  *C12M 1/00* (2006.01)
  *G01N 35/00* (2006.01)

(52) U.S. Cl.
  CPC ............... *C12M 99/00* (2013.01); *C12Q 1/18* (2013.01); *G01N 35/04* (2013.01); *B01L 2200/16* (2013.01); *B01L 2300/0609* (2013.01); *B01L 2300/0803* (2013.01); *B01L 2300/1894* (2013.01); *G01N 2035/00445* (2013.01); *G01N 2035/0443* (2013.01); *G01N 2035/0465* (2013.01)

(58) Field of Classification Search
  CPC ............. G01N 2035/0465; B01L 3/527; B01L 2200/16; B01L 2300/009; B01L 2300/0803; B01L 2300/1894; C12M 23/48; C12M 99/00; C12M 41/12; C12Q 1/18
  See application file for complete search history.

DEVICE FOR THE STORAGE AND SELECTION OF PRE-FILLED CARTRIDGES OF REACTIVE DISCS

RELATED APPLICATION

This application is a National Phase of PCT/FR2015/052900, filed on Oct. 28, 2015 which in turn claims the benefit of priority from French Patent Application No. 14 60562, filed on Nov. 3, 2016, the entirety of which are incorporated by reference.

BACKGROUND

Field of the Invention

The present invention concerns a device for storage and selection, notably for the storage and selection of cartridges that are prefilled with reagent disks to be placed on a support such as a culture medium, as well as an assembly comprising a plurality of cartridges that are prefilled with reagent disks to be placed on a support such as a culture medium, and a device of the aforementioned type.

More particularly it concerns a device for storage and selection, comprising:
  a plurality of magazines each able to store a cartridge of disks,
  at least one magazine holding support,
and for each support, driving means for driving the movement of said magazine holding support.

Description of Related Art

Prefilled cartridges of reagent disks, that is to say, disks impregnated with an active substance, such as an antibiotic or an antifungal and used for example for testing the sensitivity of microorganisms to said active substance, are well known to a person skilled in the art.

The purpose of these sensitivity tests is to identify the active substance or substances which are able to kill or inhibit the growth of microorganisms in a sample to be tested.

In practice, the sample to be tested is placed on a culture medium, such as an agar in a Petri dish, and the disks are placed on said agar. After incubation, the sensitivity can be determined visually by the appearance around the placed disk.

Up to now, the placing of these disks on the culture medium has been done either manually, using a distributor of the type as described in the international patent application WO 2006/109005, or automatically with the aid, for example, of an installation of the kind as described in the European patent EP 2.518.136.

However, these devices still leave doubt as to the effectiveness of the test performed. In fact, these manual or automatic distributors are meant to distribute various disks, each one having a different active substance which is temperature-sensitive.

Thus far, in the case of a manual distributor which is stored in a refrigerator, the distributor is taken out from the refrigerator during each placement operation. There is thus a risk of forgetting to place the distributor in the refrigerator after its use, so that all or some of the disks may be damaged on account of deterioration of the properties of the active substances, since an exposure to too high a temperature cannot be ruled out. It is the same with the automatic distributor whereby the wheel of the distributor needs to be dismantled after each use.

OBJECTS AND SUMMARY

One purpose of the present invention is thus to propose a device for storage and selection of the aforementioned type whose design is able to guarantee the relevance of the tests to be performed without detracting from the possibilities of single or multiple depositions and automatic depositions of said disks.

Accordingly, the subject matter of the invention is a device for storage and selection, notably for the storage and selection of cartridges that are prefilled with reagent disks to be placed on a support such as a culture medium, said device comprising:
  a plurality of magazines each able to store a cartridge of disks,
  at least one magazine holding support,
  and for each support, driving means for driving the movement of said magazine holding support,
  characterized in that the device comprises a chamber configured to house at least one magazine holding support in the usage configuration of the device, said chamber being provided with a cooler of its interior volume, and at least one so-called placement opening facing which the driving means for driving the movement of a magazine holding support are configured to position at least one magazine of said support in a so-called placement configuration of said magazine, and in that the device comprises a drive mechanism for driving the movement of the magazine in placement configuration between a position where said magazine is distant from and a position closer to the placement opening of the chamber.

Thanks to the presence of at least one closed chamber provided with a cooler, inside which at least one magazine holding support can be stored, including in the usage configuration, that is to say, during the operation of the device, and thanks to the design of the magazine holding support, it is no longer necessary after each use to move the magazine holding support to a non-hostile atmosphere, so that the relevance of the tests to be performed due to the quality of the reagents can be guaranteed.

Preferably, the drive mechanism for driving the movement of the magazine in placement configuration between a position of said magazine away from and a position close to the placement opening of the chamber is housed at least partially inside the chamber. The result is a compact placement device.

Preferably, the drive mechanism for driving the movement of the magazine in placement configuration between a position of said magazine away from and a position close to the placement opening of the chamber comprises a pusher for moving said magazine from the position away from the placement opening of the chamber to a position close to the placement opening of the chamber and means for returning said magazine to the position away from the placement opening, said pusher acting against said return means.

Preferably, the pusher and the return means are housed at least partially inside the chamber.

This results in an extremely simple mechanism with slight risk of malfunction and whose reduced bulk allows the positioning of said driving means inside the chamber.

The return means comprise at least one elastically deformable element, such as a spring or a rubber block.

Preferably, the chamber is provided with at least one so-called cartridge loading/unloading opening opposite which the driving means for driving the movement of a magazine holding support are configured to position a magazine of said support in a so-called loading/unloading configuration of said magazine, and the device comprises a drive mechanism for driving the movement of the magazine in loading/unloading configuration between a position of said magazine away from and a position close to the loading/unloading opening of the chamber.

Preferably, the drive mechanism for driving the movement of the magazine in loading/unloading configuration between a position of said magazine away from and a position close to the loading/unloading opening of the chamber is housed at least partially inside the chamber.

It is thus possible to load/unload each magazine with cartridges without having to take the support out from the chamber.

Preferably, the loading/unloading opening is an opening different from the placement opening.

As a result, when there are a plurality of supports present inside the chamber, it is possible to load/unload a support while another support is undergoing a placement operation. It is likewise possible to position the cartridge loading/unloading opening at a place in the chamber which is easily accessible to the operator.

Preferably, the loading/unloading opening is an opening which can be closed by a closing element.

Such a closing element makes it possible to reduce the energy costs associated with the presence of the cooling means.

Preferably, the placement opening is an opening which can be at least partly closed by a placement device.

Thus, the placement device is positioned outside of the chamber to make it easily accessible.

Preferably, the drive mechanism for driving the movement of the magazine in loading/unloading configuration between a position of said magazine away from and a position close to the loading/unloading opening of the chamber comprises a pusher for moving said magazine from the position away from the loading/unloading opening of the chamber to a position close to the loading/unloading opening of the chamber and means for returning said magazine to the position away from the loading/unloading opening, the pusher acting against said return means.

Once again, the return means comprise at least one elastically deformable element, such as a spring or a rubber block.

Preferably, each magazine is in the form of a tubular body, at least one of whose ends, known as the loading/unloading end, is an open end to allow an axial loading/unloading of cartridges of said magazine.

Advantageously, at least the magazine in placement configuration, preferably each magazine, is mounted on the support able to slide along a guideway carried by the support.

Advantageously, the magazine holding support, or at least one of them, preferably each of them, is a magazine holding wheel and the driving means for driving the movement of said magazine holding support are driving means for driving a rotation.

Preferably, each magazine holding wheel is, when housed in said chamber, a wheel said to have a horizontal axis of rotation which extends in the upright state with the magazines of said wheel disposed in a spokelike arrangement, and with their so-called open loading/unloading end turned toward the outside of the wheel, and at least the magazine in placement configuration is mounted able to slide along a guideway carried by the wheel and radially to the axis of rotation of the wheel.

This arrangement facilitates the loading and unloading of cartridges, as well as a later automatic placement. Furthermore, this arrangement allows the use of standard placement devices with a classical configuration.

Preferably, the tubular body of said magazine is a body at least partly elastically deformable provided on the inside with a locking tab.

Preferably, the tubular body of said magazine is provided on the inside with an end stop formed by a narrowing of the clear cross section of said body.

The result is a precise and certain positioning of a cartridge inside the magazine.

Preferably the chamber is configured to house at least two magazine holding supports, the driving means for driving the rotation of a magazine holding support are distinct from one magazine holding support to another so as to allow an independent driving in rotation of each of the magazine holding supports.

Thanks to this arrangement, it is possible to deposit at least two disks in parallel and to store a large number of types of disks.

Preferably, the chamber is provided with ventilation means.

The invention further relates to an assembly of the type comprising a plurality of cartridges that are prefilled with reagent disks to be placed on a support such as a culture medium, and a device for the storage and selection of said cartridges, said device comprising:

a plurality of magazines each in the form of a tubular body, blind or through, and each configured to store a cartridge of disks, at least one magazine holding support, and for each support, driving means for driving the movement of said magazine holding support, characterized in that the device is according to the one described above and in that the assembly formed by the cartridge and the magazine in placement configuration extends, in the position of said magazine close to the placement opening, at least partly projecting from the chamber through said placement opening.

Preferably, each cartridge is, in the stored state in said magazine, threaded in said magazine in a position in which the open end for distribution of disks of the elongated body constituting the cartridge extends flush or projecting from the open end or ends of the tubular body of the magazine forming the so-called loading/unloading end of the magazine, through which the magazine is able to be loaded/unloaded axially with cartridges, and at least the open end for distribution of disks from the cartridge of the magazine in the placement configuration projects from the placement opening of the device in the position of said magazine close to the placement opening of the chamber.

BRIEF DESCRIPTION OF THE DRAWINGS

The invention will be better understood upon reading the following description of sample embodiments, making reference to the enclosed drawings, in which.

DETAILED DESCRIPTION

Figure 1:
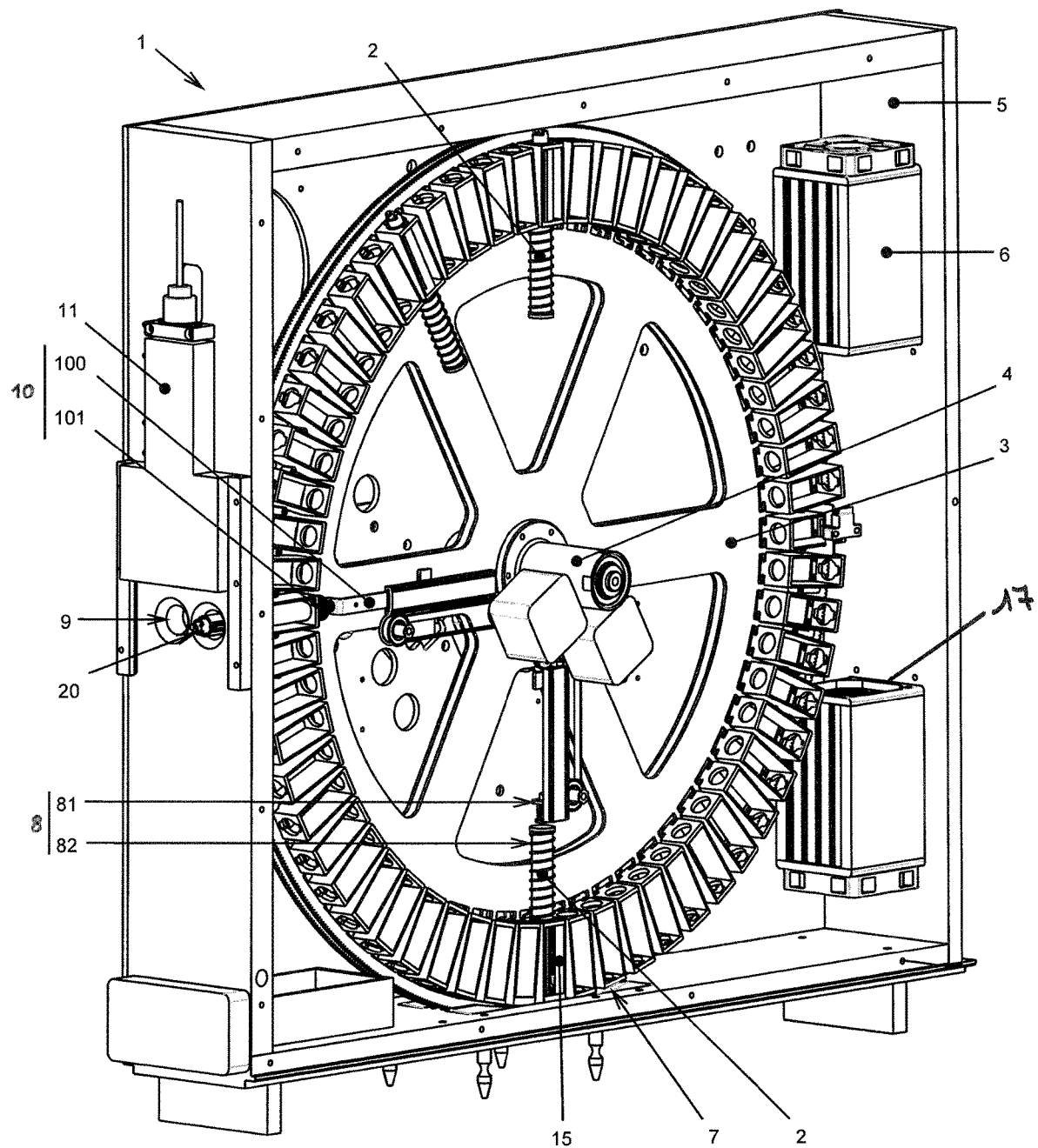
FIG. 1 is a partial perspective view of a device according to the invention, the front face of the chamber having been omitted for better viewing of the magazine holding wheel and only four magazines being shown for a less cluttered drawing.
Figure 2:
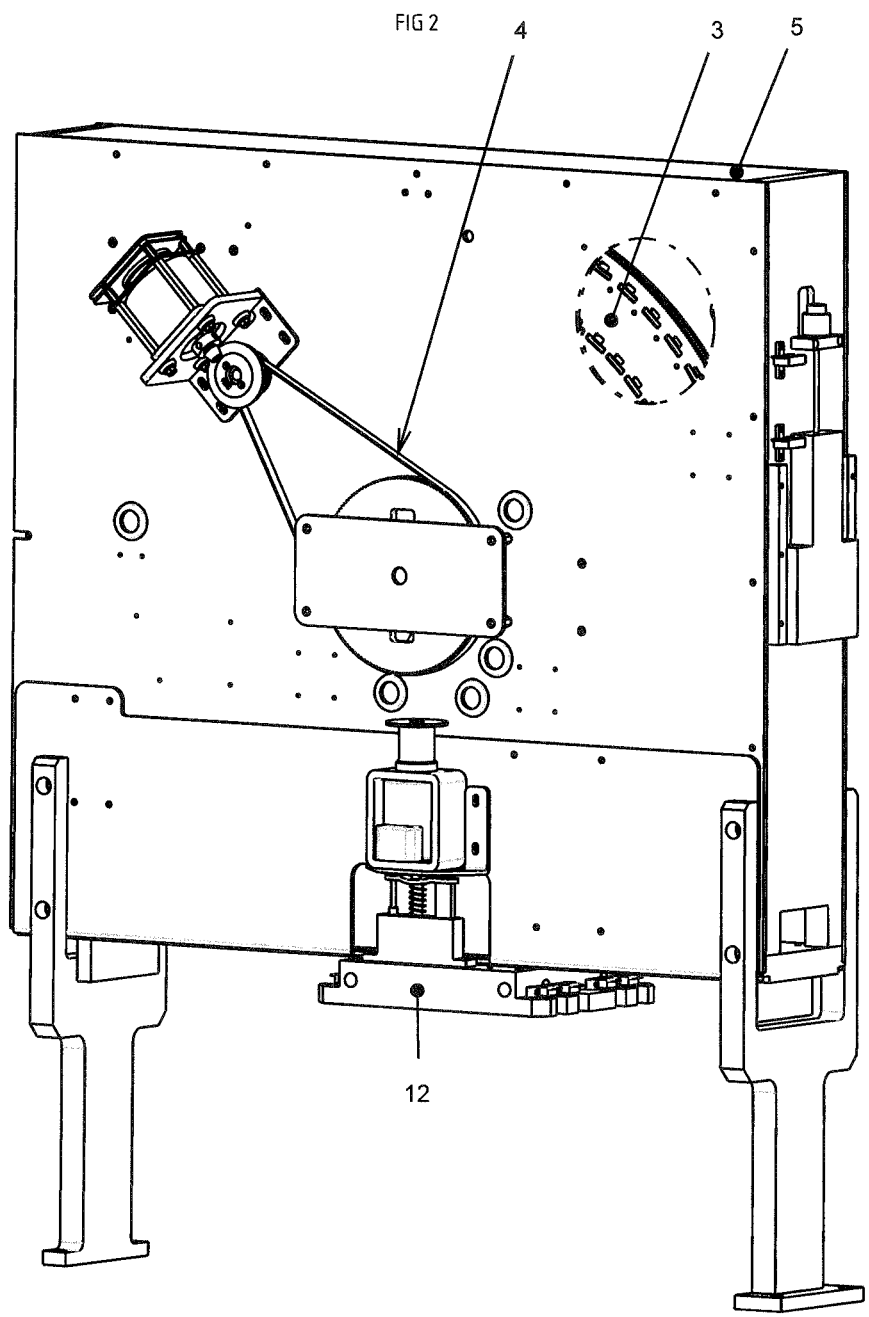
FIG. 2 is a rear view of a device according to the invention.
Figure 3:
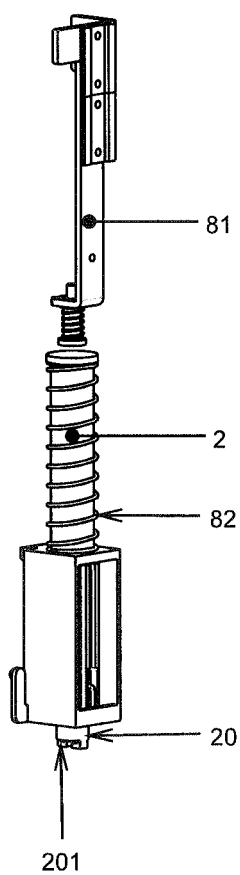
FIG. 3 is a perspective view of a magazine loaded with cartridges, of its means of connection to the wheel, and of its drive mechanism for driving the movement, said magazine being represented in a position corresponding to the position occupied in the position away from the placement or loading/unloading opening.
Figure 4:
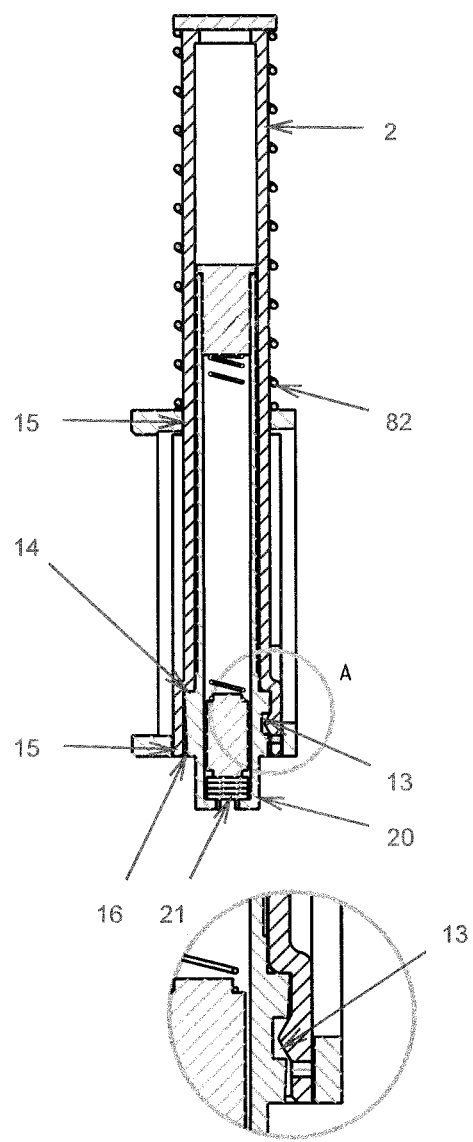
FIG. 4 is a cross-sectional view of the magazine loaded with cartridges of FIG. 3 with a detail view of the holding of the cartridge in the magazine.
Figure 5:
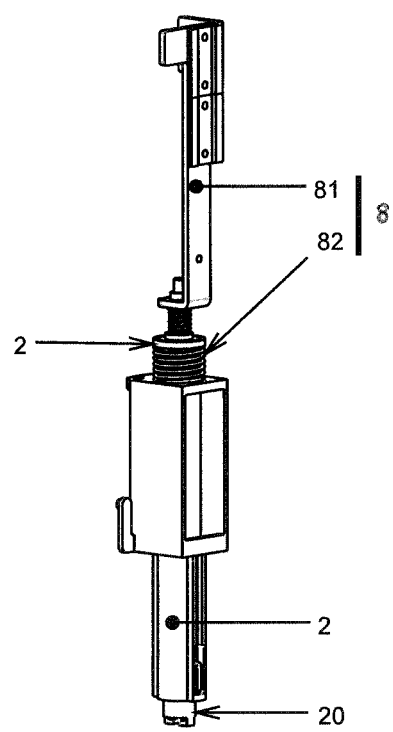
FIG. 5 is a perspective view of a magazine loaded with cartridges, of its means of connection to the wheel, and of its drive mechanism for driving the movement, said magazine being represented in a position corresponding to the position occupied in the position close to the placement or loading/unloading opening.
Figure 6:
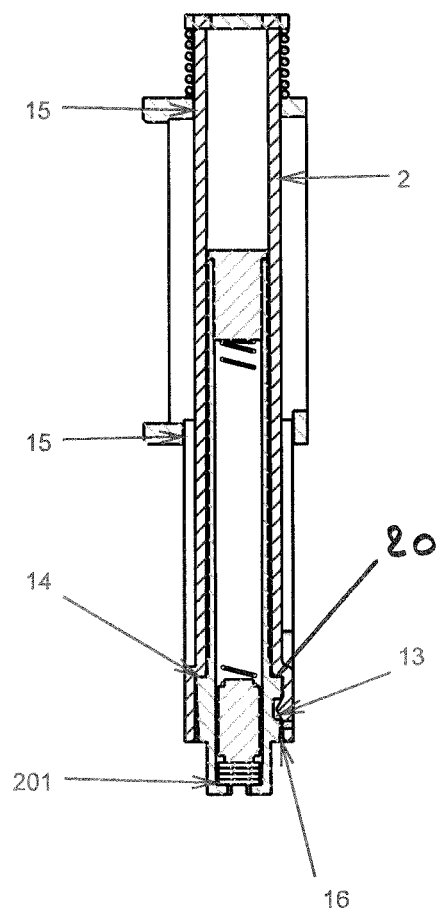
FIG. 6 is a cross-sectional view of the magazine loaded with cartridges of FIG. 5.

As mentioned above, the subject of the invention is a device 1 for storage and selection, notably for the storage and the selection of cartridges 20 which are prefilled with reagent disks 21 to be placed on a support, such as a culture medium, as well as an assembly comprising such a device 1 and a plurality of prefilled cartridges 20 of reagent disks 21 to be placed on a support such as a culture medium.

As mentioned above, the cartridges 20 which can be used are well known to those skilled in the art. Each cartridge 20 is in the form of an elongated blind tubular body, inside which the disks are stacked from the closed end to the open end 201, or distribution end of disks from said body, with the interpositioning between the disk closest to the closed end and said closed end of a spring-loaded pusher to move the stack of disks in the direction of the open end of the cartridge.

This open end 201 of the cartridge is provided with claws for holding the disks inside the cartridge against the action of the pusher, these claws bounding radial openings in the area of said open end through which the disks can be expelled one by one from the cartridge.

Generally the disks of the same cartridge are identical from one disk to another, that is to say, they carry the same active substance. It should be noted that the term "disk" should be taken in its broadest meaning and should include a pastille, and in particular it may apply to a shape not perfectly circular or a thickness which is not constant.

In the example shown in the figures, the tubular body making up the cartridge 20 is a steplike portion provided, from its closed end to its open end, with an external peripheral shoulder whose role shall be described below, and having in the steplike portion of larger cross section a recess whose role will likewise be described below.

The reagent disks 21, that is to say, loaded with active substance, which are contained inside such a cartridge may be disks whose active substance is an antibiotic, an antifungal, or something else.

As for itself, the device 1 which makes it possible to store and select cartridges 20 of the aforementioned type, comprises a plurality of magazines 2, each of which can store a cartridge 20 of disks, and at least one support 3, in the present case a wheel 3, known as a magazine holding wheel, on which the magazines are arranged. In the following, each support 3 is a wheel. Of course, one could also contemplate for example a magazine holding support 3 in the form of an elongated body, actuated for example by a reciprocating motion with the magazines arranged side by side on said support.

In the example shown, each magazine 2 is in the form of a tubular body, at least one of whose ends, known as the loading/unloading end, is an open end 16 to allow an axial loading/unloading of cartridges in said magazine. Each magazine is thus configured, i.e., dimensioned and shaped to receive in a sliding nesting a cartridge introduced axially in said magazine by its open end 16.

Each cartridge 20 in the stored state in said magazine 2 is thus threaded inside said magazine in a position in which the open end 201 for distribution of disks from the elongated body making up the cartridge 20 extends flush with or projecting from the open end 16 of the tubular body of the magazine forming the loading/unloading end of the magazine by which the magazine 2 can be loaded/unloaded with cartridges.

To enable the cartridge to be held partly nested in the magazine, the tubular body of the magazine 2 is a body which is at least partly elastically deformable, provided on the inside with a locking tab 13. This locking tab 13 is able to cooperate with the recess devised in the area of the steplike portion of the cartridge as described above.

The tubular body of the magazine 2 is furthermore provided on the inside with an end stop 14 formed by a narrowing of the clear cross section of said body. This narrowing of the clear cross section operates from the open end 16 of said magazine in the direction of its opposite end. This narrowing of the clear cross section forms a surface against which the steplike portion of larger cross section of the cartridge can bear in the state of the cartridge inserted in the magazine to enable a certain and precise positioning of the cartridge inside the magazine.

In the example represented, the magazines 2 are mounted on the wheel in spokelike arrangement with their open end 16, or loading/unloading end, turned toward the outside, that is, the external circumferential rim of the wheel, and each magazine 2 is mounted so that it can slide along a guideway 15 carried by the wheel 3, this guideway being disposed radially to the axis of rotation of the wheel.

This guideway 15 is delimited here each time by a static through sheath arranged on the wheel.

The device also comprises, for each magazine holding wheel 3, driving means 4 for driving the rotation of the wheel comprising at least one motor. These driving means 4 for driving the rotation of the wheel are means controlled by a control unit able to receive, in a manner known in itself, information coming from data acquisition means. The details of this control process will not be described here, because they are well known to a person skilled in the art.

In the example shown, each cartridge is furnished with an identification code which can be read by a reader disposed in a location of the device able to provide a referencing of the position of each cartridge in the magazines. Thus, the code reader can be disposed at the level of the loading/unloading opening for cartridges of the device, which will be described below. In parallel, a cartridge selection program can be entered manually in the control unit which, using this data, is able to steer the driving means for driving the rotation of the wheel.

Finally, the device comprises a chamber 5 configured to house at least one magazine holding wheel 3 in the configuration of use, that is to say, the functioning configuration of the device.

In the example shown, the chamber 5 is adapted to house at least two magazine holding wheels 3 and the driving means 4 for driving the rotation of a wheel are distinct from the driving means 4 for driving the rotation of the other wheel, so as to allow an independent driving of the rotation of each of the magazine holding wheels 3. The two magazine holding wheels 3 are in a parallel arrangement inside the chamber.

The chamber 5 is in the form of a box of parallelepiped shape, comprising a top face, a bottom face, a front face, a rear face and two lateral faces. This chamber 5 is provided with a cooler 6 for its interior volume able to maintain the temperature inside the volume delimited by said chamber below a predetermined value.

This cooler 6 can be controlled as a function of the temperature prevailing inside the chamber.

Thus, the chamber may comprise temperature measurement means and means of control of the cooler as a function of said temperature. The cooler may likewise be programmed to operate for certain periods without measuring the temperature.

This cooler 6 is formed here by Peltier effect modules housed inside the chamber. This cooler 6 may, in an equivalent manner, comprise a refrigerator of compression type, a refrigerator of absorption type, an air type cooler, a water type cooler, a heat exchanger, a heat pump, eutectic salts, or another type.

The chamber 5 may furthermore comprise at least one fan and a sensor to measure the hygrometry level inside the chamber to maintain the inside of the chamber at an acceptable hygrometry level.

In order to allow access to the contents of the chamber, this chamber is provided with at least one so-called placement opening 7 opposite which the driving means 4 for driving the rotation of a magazine holding wheel 3 are configured to position at least one magazine of said wheel in the so-called placement configuration of said magazine.

In the example shown, this placement opening 7 is devised in the area of the bottom face of the chamber substantially perpendicular to the axis of rotation of the wheels. In fact, each magazine holding wheel 3 in the state when housed in said chamber 5 is a wheel said to be of horizontal axis of rotation which extends in the upright state with the magazines 2 of said wheel in a spokelike arrangement, as already mentioned above.

The device furthermore comprises a drive mechanism 8 for driving the movement of the magazine 2 in the placement configuration, that is, in the condition pre-positioned opposite the placement opening, between a position away from the placement opening 7 of the chamber 5 and a position close to the placement opening 7 of the chamber to enable, in the position of the magazine close to the placement opening 7 of the chamber, at least at the open end 201 for distribution of disks from the cartridge 20 of said magazine, an extension projecting from the placement opening 7 of the device to enable a subsequent placing, by a placement device 12, of a disk of the cartridge housed inside said magazine.

For this purpose, the placement opening 7 is an opening which can be at least partly closed by the placement device 12. This placement device 12 is here positioned beneath the chamber, applied to the bottom face of the chamber. This placement device 12 can be a placement device known in itself and comprising on the one hand a radial element for ejecting a disk from the cartridge, this ejecting element being radially movable in the area of the free end of the cartridge in order to extract a disk from the cartridge through the radial openings of the cartridge, and on the other hand a pusher, for example, which once the disk has emerged from the cartridge accompanies the dropping of the disk onto a support, such as a Petri dish, disposed beneath the chamber perpendicular to the placement opening 7.

Once the placement has been done, the magazine in so-called placement configuration can be returned to the position away from the placement opening in order to allow the return of the magazine and its cartridge to the inside of the chamber.

Thus, the assembly formed by the cartridge 20 and the magazine 2 in placement configuration extends, in the position of the magazine 2 close to the placement opening 7, at least partly projecting from the chamber through said placement opening 7, while in the position away from the placement opening 7, this assembly is disposed inside the chamber to enable a rotation of the magazine holding wheel.

In the example shown, the drive mechanism 8 for driving the movement of the magazine 2 in placement configuration between a position of said magazine 2 away from and a position close to the placement opening 7 of the chamber is housed inside the chamber and comprises a pusher 81 for the movement of said magazine 2 from the position away from the placement opening 7 of the chamber 5 to a position close to the placement opening 7 of the chamber 5 and means of return 82 for returning said magazine 2 to the position away from the placement opening 7, said pusher 81 operating against said return means 82.

The pusher 81 here is in the form of a rod mounted with the help of a motor able to move back and forth in a direction radial to the axis of rotation of the wheel in the direction of moving away from and moving closer to the axis of rotation of the wheel.

This rod is disposed in the alignment of the magazine, in placement configuration, between the axis of rotation of the wheel and said magazine.

As for the return means 82, these are in the form of a helical spring wound about the tubular body of the magazine and bearing on the one hand against an external peripheral shoulder of the magazine, and on the other hand against the wheel. This helical spring returns the magazine, able to slide along its guideway 15 carried by the wheel, to the position away from the placement opening.

The operation of this drive mechanism 8 for driving the movement of the magazine 2 in placement configuration between a position away from and a position close to the placement opening 7 is as follows:

Once the magazine 2 is in placement configuration, that is to say, prepositioned opposite the placement opening, the pusher is moved in the direction of the outside of the wheel, that is to say, in the direction coming closer to the placement opening. In the course of this movement, it acts by thrusting against the magazine which tends, by its return means 82, to resist the action of the pusher. The magazine 2 is moved by the pusher 81 as far as the position in which the assembly formed by the cartridge and said magazine projects from the chamber through the placement opening 7. It should be noted that by "position projecting from the chamber of said assembly" is meant that the cartridge can project from said chamber alone or in cooperation with the magazine.

When the placement as described above has taken place, the pusher is moved in the direction of the axis of rotation of the wheel, that is to say, in the direction moving away from the placement opening, and the assembly formed by the magazine and the cartridge may, under the action of the return means 82, return to the position inside the chamber.

A new placement can then be achieved with the help of the drive mechanism 8 for driving the movement of the magazine after a possible rotation of the wheel to position a new magazine in the placement configuration.

To complete this device, the chamber 5 is provided with at least one so-called cartridge loading/unloading opening 9 opposite which the driving means 4 for driving the rotation of a magazine holding wheel 3 are configured to position a magazine 2 of said wheel 3 in a so-called loading/unloading configuration of said magazine 2, and the device 1 comprises a drive mechanism 10 for driving the movement of the magazine 2 in loading/unloading configuration between a position of said magazine 2 away from and a position close to the loading/unloading opening 9 of the chamber 5.

In fact, one could contemplate removing the wheel from the chamber to enable it to be loaded/unloaded with cartridges. However, to reduce the number of manipulations of the wheel and enable a rapid replacement of a cartridge, the loading/unloading of cartridges of the wheel with the wheel housed inside the chamber is preferred.

In the example shown, the loading/unloading opening 9 is an opening distinct from the placement opening 7. This loading/unloading opening 9 is arranged on a different face of the chamber from the one having the placement opening 7.

In the example shown, this loading/unloading opening 9 is disposed on a lateral face of the chamber, that is to say, a face of the chamber which extends at right angles to the bottom face of the chamber, this bottom face having the placement opening 7.

The loading/unloading opening 9 is an opening which can be closed by a closure element 11.

In the example shown, this closure element 11 is formed by guillotine hatch arranged outside the chamber. This closure element 11 is thus moved into an open position of the loading/unloading opening 9 when it is necessary to carry out a loading of full cartridges of the magazines or an unloading of generally empty cartridges from the magazines.

In the example shown, the drive mechanism 10 for driving the movement of the magazine 2 in loading/unloading configuration between a position of said magazine 2 away from and a position close to the loading/unloading opening 9 of the chamber 5 is housed inside the chamber 5 and comprises a pusher 100 for moving said magazine 2 from the position away from the loading/unloading opening 9 of the chamber 5 to a position close to the loading/unloading opening 9 of the chamber 5 and return means 101 for returning said magazine 2 to the position away from the loading/unloading opening 9, the pusher 100 acting against said return means 101.

The operation of the pusher and the return means is identical to that described for the drive mechanism 8 for driving the movement of the magazine in placement configuration. Thus, the pusher 100 here is once again present in the form of a rod disposed in an alignment of the magazine in loading/unloading configuration between the axis of rotation of the wheel and said magazine. This rod is able to move back and forth in a direction radial to the axis of rotation of the wheel in the sense of a movement away from and close to the axis of rotation of the wheel.

As for the return means 101, these are in the form of a helical spring wound about the tubular body of the magazine and bearing on the one hand against an external peripheral shoulder of the magazine, and on the other hand against the wheel. This helical spring returns the magazine, able to slide along its guideway 15 carried by the wheel, to the position away from the loading/unloading opening.

It should be noted that the spring forming the return means 82 of the magazine, in placement configuration, to the position away from the placement opening 7 is the same as the spring forming the return means of the magazine in loading/unloading configuration to the position away from the loading/unloading opening 9. This results in a simplification of the assembly. In fact, in the example shown, each magazine 2 is able to slide along a guideway 15 and is fitted with return means close to the axis of rotation of the wheel, that is, the position away from the placement and the loading/unloading openings.

As for the pushers, they are distinct and the rods of said pushers form substantially a right angle between them.

The operation of this drive mechanism 10 for driving the movement of the magazine 2 in loading/unloading configuration between a position away from and a position close to the loading/unloading opening 9 is as follows:

Once the magazine 2 is in loading/unloading configuration, that is to say, prepositioned opposite the loading/unloading opening 9, the pusher is moved in the direction of the loading/unloading opening, that is to say, in the direction getting closer to the outside of the wheel.

In the course of this movement, it acts by thrusting against the magazine which tends, by its return means 101, to resist the action of the pusher. The magazine 2 is moved by the pusher as far as the position in which the assembly formed by the cartridge and said magazine projects from the chamber through the loading/unloading opening 9.

It should be noted that once again by "position projecting from the chamber of said assembly" is meant that the cartridge can project from said chamber alone or in cooperation with the magazine.

When the loading/unloading as described above has taken place, the pusher is moved in the direction of the axis of rotation of the wheel, that is to say, in the direction moving away from the loading/unloading opening, and the assembly formed by the magazine and the cartridge may, under the action of the return means 101, return to the position inside the chamber.

In the position of the magazine close to the loading/unloading opening, the loading or respectively the unloading of cartridges from the magazine is done manually. For the loading, the cartridge is inserted by its closed end into the loading/unloading opening 10 and then introduced axially by sliding nesting in the magazine until an end stop position thanks to the aforementioned shoulder of the magazine.

When the magazine is configured to project from the chamber through the loading/unloading opening 9 in the position close to the loading/unloading opening 9, in this case the cartridge is introduced manually directly into said magazine.

For an unloading, it is enough simply to exert a traction on the portion of the cartridge projecting from the magazine, that is to say, on the open end 201 for distribution of disks of the elongated body making up the cartridge in the position of said magazine close to the loading/unloading opening 9.

The loading or respectively the unloading of cartridges from the device should thus take a brief time.

Furthermore, when one has two parallel wheels, one can carry out the loading or respectively the unloading of cartridges in one wheel in parallel with a placement operation of the other wheel.

The invention claimed is:
1. A device for storage and selection of cartridges that are prefilled with reagent disks to be placed on a culture medium, said device comprising:

a plurality of magazines each able to store a cartridge of reagent disks, a rotationally movable magazine holding support for supporting said plurality of magazines and a drive for driving the rotational movement of said magazine holding support, wherein the device has a refrigerated cooling chamber configured to house said magazine holding support, and said magazines each have at least one placement opening face through which said reagent disks are dispensed, where the drive for driving the rotational movement of said magazine holding support positions a placement opening face of one of said magazines of said magazine holding support in a placement configuration, where, while holding said magazine holding support in position with said magazine in said placement configuration, the magazine holding support further comprises a drive mechanism for driving the movement of the magazine and its opening face, between a first position where said magazine is away from and a second position where said opening face of said magazine is close to a placement opening of the chamber, allowing said reagent disk to be dispensed from said opening face of said magazine through said placement opening onto said culture medium.

2. The device as claimed in claim 1, wherein the drive mechanism for driving the movement of the magazine is a pusher for moving said magazine from the position away from the placement opening of the chamber to a position close to the placement opening of the chamber and means for returning said magazine to the position away from the placement opening, said pusher acting against said means of return.

3. The device as claimed in claim 1, wherein the refrigerated cooling chamber is further provided with at least one additional opening, referred to as a cartridge loading/unloading opening, where said drive positions a magazine of said magazine holding support in a loading/unloading configuration of said magazine, and wherein the drive mechanism drives the movement of the magazine, in the loading/unloading configuration, between a position of said magazine away from, and a position close to said cartridge loading/unloading opening of the chamber.

4. The device as claimed in claim 3, wherein the loading/unloading opening is an opening different from the placement opening.

5. The device as claimed in claim 3, wherein the loading/unloading opening is an opening which can be closed by a closing element and wherein the placement opening is an opening which can be at least partly closed by a placement device.

6. The device as claimed in claim 3, wherein the drive mechanism for driving the movement of the magazine in the loading/unloading configuration between a position of said magazine away from and a position close to the loading/unloading opening of the chamber is a pusher for moving said magazine from the position away from the loading/unloading opening of the refrigerated cooling chamber to a position close to the loading/unloading opening of the chamber and means for returning said magazine to the position away from the loading/unloading opening, said pusher acting against said return means.

7. The device as claimed in claim 1, wherein each of said magazines are in the form of a tubular body, at least one of whose ends is a loading/unloading end that is an open end to allow an axial loading/unloading of cartridges from said magazine.

8. The device as claimed in claim 7, wherein a magazine in the placement configuration is mounted on the magazine holding support, able to slide along a guideway carried by the magazine holding support.

9. The device as claimed in claim 1, wherein the magazine holding support is a wheel and in that the drive for driving the movement of said magazine holding support is a drive for driving a rotation of the wheel.

10. The device as claimed in claim 9, wherein either each magazine is in the form of a tubular body, at least one of whose ends, is a loading/unloading end that is an open end to allow an axial loading/unloading of cartridges from said magazine; or in placement configuration each magazine is mounted on the magazine holding support is able to slide along a guideway carried by the magazine holding support, wherein said magazine holding support is, when housed in said chamber, a wheel having horizontal axis of rotation with the magazines of said wheel disposed in a spokelike arrangement, and with their open loading/unloading ends facing an outside of the wheel, and wherein at least the magazine in the placement configuration is mounted able to slide along a guideway carried by the wheel, and radially relative to an axis of rotation of the wheel.

11. The device as claimed in claim 7, wherein the tubular body of said magazine is a body, at least partly elastically deformable, provided on its inside with a locking tab.

12. The device as claimed in claim 7, wherein the tubular body of said magazine is provided on its inside with an end stop formed by a narrowing of a clear cross section of said body.

13. A device comprising:

Assemblies, each having one of a plurality of cartridges that are prefilled with reagent disks to be placed on a culture medium, said cartridges each disposed within a magazine, the combined cartridges and magazines forming said assemblies, and being within saki device for the storage and selection of said cartridges, said device comprising:

said plurality of magazines each in the form of a tubular body, with a clear cross-section, and each configured to store one of said cartridges of reagent disks, a rotationally movable magazine holding support for supporting said magazines, and a drive for driving the rotational movement of said magazine holding support, wherein the device has a refrigerated cooling chamber configured to house said magazine holding support, each of said magazines having at least one placement opening face through which said reagent disks are dispensed, where said drive of said magazine holding support positions at least one assembly of a magazine and cartridge therein, of said magazine holding support, in a placement configuration, and, while holding said magazine holding support in position with said at least one assembly in said placement configuration, said magazine holding support comprises a drive mechanism for driving the movement of the at least one assembly and an opening face of magazine thereof, between a first position where said at least one assembly is away from and a second position where said opening face of said magazine of said at least one assembly is close to a placement opening of the chamber, allowing said reagent disk to be dispensed from said opening face of said magazine of said at least one assembly through said placement opening onto said culture medium, and in that in the position of said at least one assembly is close to the placement opening, said at least one assembly of said magazine and cartridge therein extends at least partly projecting from the chamber through said placement opening.

14. The assembly as claimed in claim 13, wherein each cartridge is, in a stored state in a said magazine of said plurality of magazines, threaded in said magazine in a position in which an open end of said magazine for the distribution of said reagent disks of an elongated body constituting the cartridge of reagent discs, extends flush or projecting from the open end of the tubular body of the magazine, through which the magazine is able to be loaded/unloaded axially with the cartridges, wherein at least the open end for the distribution of disks from the cartridge projects from the placement opening of the chamber when said magazine is in the position of said magazine close to the placement opening of the chamber.

* * * * *